United States Patent
Duineveld et al.

(10) Patent No.: US 8,827,700 B2
(45) Date of Patent: Sep. 9, 2014

(54) SPRAYHEAD APPARATUS FOR GENERATING A GAS-ASSISTED DROPLET SPRAY FOR USE IN ORAL CLEANING

(75) Inventors: Paulus Cornelis Duineveld, Drachten (NL); Alexandra Kulas, Sammarnish, WA (US); Martinus Bernardus Stapelbroek, Rolde (NL); Jasper Zuidervaart, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 584 days.

(21) Appl. No.: 12/303,149

(22) PCT Filed: Jun. 25, 2007

(86) PCT No.: PCT/IB2007/052454
§ 371 (c)(1),
(2), (4) Date: Dec. 2, 2008

(87) PCT Pub. No.: WO2008/001301
PCT Pub. Date: Jan. 3, 2008

(65) Prior Publication Data
US 2009/0239192 A1    Sep. 24, 2009

Related U.S. Application Data

(60) Provisional application No. 60/817,218, filed on Jun. 27, 2006.

(51) Int. Cl.
*A61C 1/02* (2006.01)
*A61H 13/00* (2006.01)

(52) U.S. Cl.
USPC .............................................. 433/80; 601/162

(58) Field of Classification Search
USPC ......... 433/80, 81, 88; 601/162, 163; 239/398, 239/290, 294, 296, 427, 589
See application file for complete search history.

(56) References Cited

U.S. PATENT DOCUMENTS

| | | | |
|---|---|---|---|
| 3,828,771 A | | 8/1974 | Gartner |
| 4,625,916 A | * | 12/1986 | Nieuwkamp et al. ......... 239/431 |
| 4,759,712 A | * | 7/1988 | Demand ........................ 433/32 |
| 4,776,794 A | * | 10/1988 | Meller .......................... 433/216 |
| 5,595,346 A | | 1/1997 | Haruch et al. |
| 5,820,373 A | * | 10/1998 | Okano et al. .................... 433/80 |
| 5,829,682 A | * | 11/1998 | Haruch ......................... 239/419 |
| 6,149,429 A | | 11/2000 | Bukowski et al. |
| 2003/0207232 A1 | * | 11/2003 | Todd et al. ...................... 433/88 |
| 2005/0175960 A1 | * | 8/2005 | Wiek et al. ..................... 433/88 |
| 2006/0097084 A1 | * | 5/2006 | Gromer et al. ................ 239/589 |

FOREIGN PATENT DOCUMENTS

| GB | 2026359 A | 2/1980 |
|---|---|---|
| WO | 2005070324 A2 | 8/2005 |

* cited by examiner

*Primary Examiner* — Heidi M Eide

(57) ABSTRACT

The sprayhead device includes a housing (60) having an orifice plate (62) therein with at least one orifice opening (64) therethrough. A liquid line (36) delivers liquid to the sprayhead, where it proceeds through the orifice opening, wherein the liquid flow rate through the orifice and the liquid pressure are sufficiently great relative to the size of the orifice that the liquid moves through the orifice as a continuous stream. Gas is delivered to the housing and gas flows to the interior of the sprayhead through at least two openings (68) in the housing. The gas streams (flows) intercept the liquid flow perpendicularly, approximately 180° apart. The velocity of the gas flows is sufficient to break up the liquid stream from the orifice into a spray of droplets of desired size and velocity, accelerating them out of an acceleration duct (66) exit portion of the housing.

5 Claims, 3 Drawing Sheets

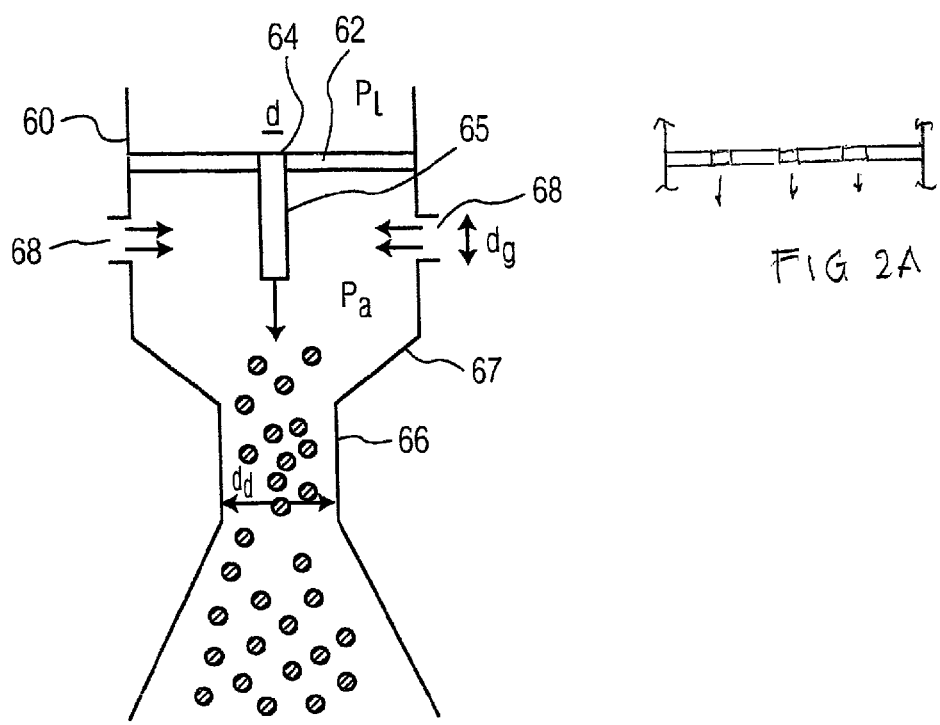
FIG. 2
FIG. 2A
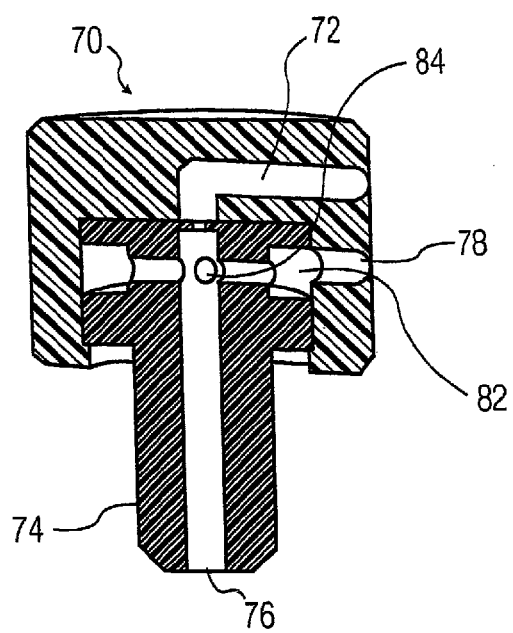
FIG. 3A

SPRAYHEAD APPARATUS FOR GENERATING A GAS-ASSISTED DROPLET SPRAY FOR USE IN ORAL CLEANING

This invention relates generally to droplet spray oral cleaning systems, and more specifically concerns a particular sprayhead arrangement for generating the droplet spray for such an oral cleaning system.

Various systems are known for generating a droplet spray in an oral cleaning apparatus. One arrangement is shown International Publication No. WO200507324, entitled "Droplet Jet System for Cleaning Teeth". In this publication, which is hereby incorporated by reference, a droplet spray is generated and the droplets accelerated by gas (air) action. The resulting droplet spray produces efficient teeth cleaning when the droplets have a velocity above 25-30 meters per second. The gas-assisted method for droplet spray generation has advantages over other droplet spray systems, including those in which liquid at high pressure is forced through a swirl nozzle to produce relatively high velocity droplets.

With gas-assisted devices, an important consideration is the configuration and size of the sprayhead member which in use fits inside the mouth; the sprayhead should fit comfortably therein and further use relatively small amounts of liquid and air in operation. These considerations are important for convenience and comfort of the user. At the same time, the apparatus must provide effective teeth cleaning.

Hence, it is desirable to have a sprayhead arrangement for generating a spray of liquid droplets in which the large majority of the droplets have a velocity above 30 meters per second, but which is configured to fit conveniently within the mouth, providing a comfortable as well as safe and effective cleaning experience for the user.

SUMMARY OF THE INVENTION

Accordingly, the present invention is a droplet spray generating apparatus for use in an oral cleaning device, comprising: a sprayhead housing having an orifice plate therein with at least one orifice opening therethrough; a liquid line system for delivering liquid to the sprayhead housing, wherein the liquid flow rate through the orifice opening is sufficiently great relative to the size of the orifice that the liquid moves through the orifice and exits therefrom as a stream of liquid; and a gas system for delivering gas to the sprayhead housing, through at least one gas opening therein, wherein the interior of the sprayhead is arranged relative to the gas flow through the gas opening such that the gas flow strikes the liquid stream from the orifice opening with a velocity and flow rate sufficient to break up the liquid stream into a spray of droplets having sufficient size and sufficient velocity, greater than 25 meters per second, to produce cleaning of the teeth.

BRIEF DESCRIPTION OF THE DRAWINGS

FIG. 2 is a cross-sectional diagram showing the sprayhead portion of the apparatus of FIG. 1.

FIG. 2A is across-sectional diagram showing an orifice plate having a plurality of orifice openings.

FIGS. 3A and 3B are diagrams showing particular embodiments of the sprayhead portion.

FIG. 1 shows a representative fluid droplet oral cleaning apparatus, shown generally at 10. The apparatus shown includes a handle portion 12 and a removable head portion 14. The handle portion includes a reservoir for liquid 16 and an air intake 18 from the atmosphere, although an internal source of gas, including compressed gas, can also be used. Pumps 20 and 22 are associated with the liquid reservoir and the air intake 18, respectively. The apparatus has an internal power source 24, such as batteries, and its operation is controlled by electron control system 26.

Figure 1:
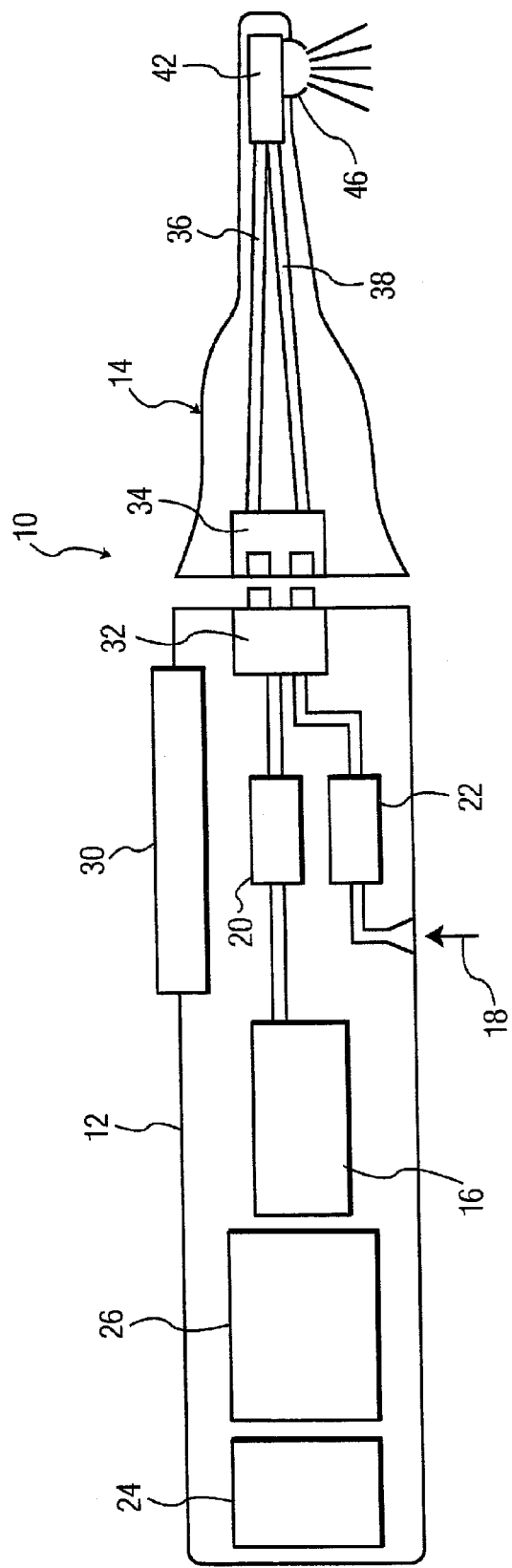
FIG. 1 is a perspective view showing in general a liquid droplet oral cleaning apparatus.
Figure 3B:
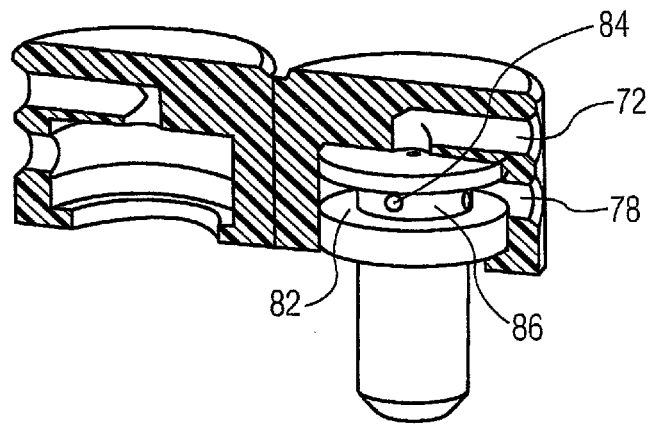
Figure 4:
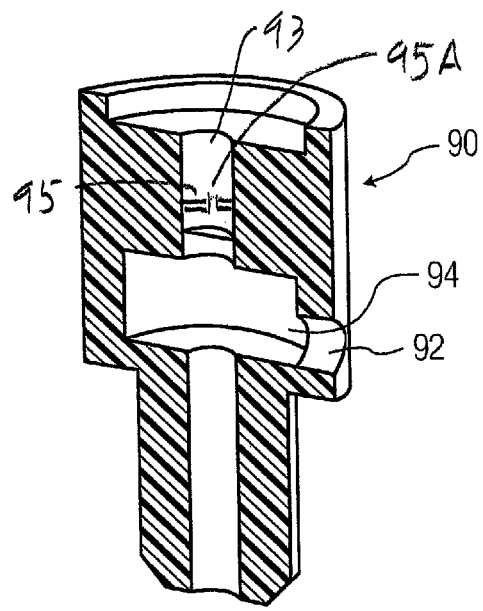
FIG. 4 shows another embodiment of the sprayhead portion.

A user interface 30, which includes an on/off switch, provides the user with the ability to control the operation of the apparatus. The handle and head include, respectively, interface portions 32 and 34, permitting the head to be conveniently removed and replaced, although a removable head portion is not essential. Liquid and gas lines 36 and 38 in the head connect to a spray generator, also referred to as a sprayhead, shown generally at 42, which includes an exit nozzle 46. A spray generator is disclosed herein which produces a droplet spray which is comfortable for the user and effective in cleaning teeth, and is of such a size and configuration that it fits conveniently within a user's mouth.

In general operation, the flow of gas in the head portion of the apparatus is directed in the sprayhead 42 to contact the liquid stream and, as a result of the impact of the gas flow on the liquid, the liquid stream is broken up into liquid droplets, as well as some remaining air and liquid in the form of streams. This mixture leaves nozzle 46 with a sufficient velocity, typically above 25-30 meters per second, and up to 70 meters per second, to effectively clean the teeth of the user. This size of the sprayhead is important, but it is also important to maintain effective control over the liquid and gas flow rates. The liquid and gas flow rates are important for the cleaning power of the resulting spray, as well as a comfortable cleaning experience for the user.

Several parameters are understood to be important in accomplishing the above desired results. These parameters include the size (diameter) d of the orifice hole for the liquid stream in the sprayhead, the size (diameter) $d_g$ of the openings for the gas stream as it is directed to the liquid stream and the size (diameter) $d_d$ of the acceleration duct, which forms the nozzle outlet of the sprayhead. Other important considerations, which will be discussed in detail below, include a minimum gas flow rate; a minimum liquid flow rate; the relationship of the minimum gas flow rate relative to the exit duct diameter; the relationship between the liquid flow rate relative to the liquid and air pressures and the diameter of the orifice for the liquid stream; and the relationship between the gas flow rate relative to the gas pressure.

FIG. 2 shows a diagram of the spray generator (sprayhead) 42. It includes a sprayhead housing 60 and an internal orifice plate 62 which has at least one opening 64 therein, through which a stream of liquid 65 is directed. The orifice plate 62 can be made of standard material, such as stainless steel, with a technique such as laser cutting or stamping used to make orifice opening 64. Other materials, such as nickel, typically with a protective coating, can be used for the orifice plate 62. The plate can also be made from plastic. Still further, the plate can be made from other materials, such as silicon or glass, with techniques from the IC industry thus being available to cut the orifice opening. These materials are resistant to many liquids, including mouthwashes. The plate is preferably between 25-500 micrometers thick, and more preferably between 100-200 micrometers.

Downstream from the orifice plate 62 in the embodiment shown are at least two opposing (approximately 180° apart) openings 68 in the housing for entrance of the gas streams. Downstream from openings 68, the housing angles inwardly at 67 to an acceleration duct portion 66, from which the liquid droplets produced by the gas action on the liquid stream exit. The gas jet openings 68 typically oppose each other and are arranged such that they hit the liquid stream from the openings at a 90° angle (perpendicular to the liquid stream). At least two opposing gas jets 68 are required; however, additional pairs of gas jets can be used. One arrangement includes a total of four gas jets, each at 90° relative to each other.

The acceleration duct 66 is typically made from an injection moldable plastic, preferably with a high contact angle, so as to minimize adherence of liquid to the acceleration duct wall. A material such as Teflon® or a coating with a fluoride component is generally preferred.

A minimum gas velocity is necessary to generate an effective fluid droplet spray. When the gas flow is below a minimum velocity, the liquid stream through opening 64 is substantially unaffected by impact with the gas and the liquid leaves the acceleration duct 66 as a straight liquid stream. When the gas stream hits the fluid stream perpendicularly within the sprayhead, at the minimum velocity or greater, sufficient pressure is exerted on the liquid stream to result in the liquid stream breaking into appropriate sized droplets, moving out of the acceleration duct 66. The minimum gas (air) velocity is provided by the formula:

$$U_g = \sqrt{\frac{4\sigma}{\rho_g d}}$$

where $\sigma$ is the surface tension of the liquid, $\rho_g$ is the gas density, d is the diameter of liquid stream through the opening in the orifice plate, and $U_g$ is the average velocity of the gas flow/jet. The relationship between the gas velocity, the number of gas inlets, and the gas flow rate is provided by the following formula:

$$Q_g = n\frac{\pi}{4}d_g^2 U_g$$

where n is the number of air inlets, $d_g$ is the diameter of the gas inlets, and $Q_g$ is the gas flow rate. This results in a minimum air flow rate of:

$$Q_g = \frac{n\pi d_g^2}{2}\sqrt{\frac{\sigma}{\rho_g d}}$$

The above indicates that the gas flow rate needed to produce the desired droplet effect increases as the diameter of the orifice in the nozzle plate for the liquid stream decreases. As one example, for an orifice of 100 μm, with four gas inlets and a water flow of 10 ml per minute, the minimum air flow rate will theoretically (with the above equation) be 2.3 liters per minute. Experimental results have been quite close to the theoretical values.

The above information results in a determination that the sprayhead should have a maximum of at most six (3 pairs) of opposed gas flow streams, with preferably two or four. Too many gas streams require too high a gas flow rate.

A minimum liquid flow rate is also necessary to generate an appropriate liquid stream from the orifice, so that liquid droplets can be produced. If the flow rate is not sufficiently high, there is no resulting stream, but rather just a sequence of drops from the orifice. As liquid flow is initiated through the orifice, pressure inside the liquid is larger than the pressure outside, as indicated:

$$P_i - P_g = \frac{4\sigma}{\alpha}$$

Thus, the basic requirement is that the pressure of the liquid flow must be substantially larger than the pressure created by the surface tension of the liquid. The required pressure is generated by the flow rate:

$$U = \alpha\sqrt{\frac{8\sigma}{\rho d}}$$

where a typical value of α is approximately 2. The relationship between the liquid flow rate, the diameter of the liquid orifice and the average liquid velocity $Q_1$ is:

$$Q_l = U\frac{\pi}{4}d^2$$

The maximum value of d (orifice diameter) then can be determined as a function of the flow rate $Q_1$ as follows:

$$d = \left[\frac{4Q_l}{\pi\alpha}\right]^{2/3}\left[\frac{\rho}{8\sigma}\right]^{1/3}$$

With a ρ of 1000 kilograms per meter, σ=0.07 N/m and α=2, a maximum orifice diameter is determined to be 0.5. Otherwise, the minimum liquid flow rate is too large to be practical or comfortable within the mouth of the user.

The acceleration of the droplets within the droplet generation device (sprayhead) is due to the velocity of the gas flow, both inside and outside the acceleration duct 66. Since it is desirable to minimize the gas flow rate for safety and comfort, it is therefore desirable to decrease the diameter $d_d$ of the acceleration duct. Preferably, this diameter is smaller than 1 millimeter, more preferably less than 0.6 millimeters, and most preferably less than 0.4 millimeters. Using a duct diameter of 0.6 mm results in an orifice opening of at most 0.35 mm for sufficient spacing between the acceleration duct wall and the liquid stream. With a duct diameter of 0.4 mm, the gas flow can be further decreased without affecting performance of the sprayhead. This results in a maximum orifice diameter of typically 150-250 micrometers.

The relationship between the liquid flow rate, the liquid pressure and the orifice diameter is also important. In this relationship, the friction due to the liquid flow into and through the sprayhead, including the orifice, is important. With a given specific orifice diameter d, the flow rate $Q_1$ of the liquid stream as a function of the gas and liquid pressures can be determined as follows:

$$Q_l = \frac{\pi}{4}d^2\sqrt{\frac{2(P_l - P_g)}{\rho_l}}\,0.82$$

The term before 0.82 is the result for frictionless flow, i.e. the maximum flow rate possible. The value 0.82 is referred to as the friction coefficient. As an example, for a diameter of 100 micrometers with a liquid pressure of 9.29 Bar and a gas pressure of 2.25 Bar, the maximum flow rate theoretical is 13.5 milliliters per minute. This is closely matched by actual experimental results. Thus, for a maximum sprayhead pressure of 8 Bar, a single orifice of 100 micrometers diameter produces approximately 13 milliliters per minute of liquid flow. To generate a higher liquid flow, multiple orifice openings are required, although typically, it is more difficult to produce a good spray with multiple orifices; and hence, a system using multiple orifices is therefore not as desirable as a single liquid orifice.

Another important relationship of sprayhead performance is the gas flow as a function of the gas and liquid pressures, the diameter of the gas opening and the size of the acceleration duct. Gas flow as a function of gas pressure is provided by the formula:

$$P_g - P_a = \frac{1}{2}\rho_l V_g^2 + h_l$$

where $h_1$ is a friction term for the liquid as it moves through the sprayhead, and $P_a$ is the atmospheric pressure.

Accordingly, the equation for the gas flow, similar to the equation for the liquid flow, is:

$$Q_g = \frac{\pi}{4} d_d^2 \sqrt{\frac{2(P_g - P_a)}{\rho_g}}\, 0.40$$

where 0.40 is a friction constant. As one example, with a gas pressure of 2.54 Bar, a theoretical gas flow ratio is 3.2 liters per minute. This, again, compares favorably with actual experimental results.

FIGS. 3A and 3B show a sprayhead arrangement in which the gas channels have a minimum number of sharp corners. The sprayhead 70 includes a liquid flow line 72 with an orifice plate having at least one orifice opening and an acceleration duct 74 with a droplet spray exit 76. A gas flow line 78 enters perpendicularly to the liquid flow line 72 and connects to a central ring opening 82. Streams of gas flow through individual channels 84 in ring wall 86 to impact the liquid stream.

FIG. 4 shows a variation, in which gas enters the sprayhead 90 through a single gas flow line 92 and then enters a circumferential ring 94 which opens directly on the liquid stream, around its entire circumference. The height of the ring 94, however, must be quite small in order to provide a sufficient air flow to adequately break up the liquid stream into the desired spray of droplets.

While the apparatus has been described in the context of an integrated hand-held unit, it should be understood that it could be used in a hand-held portion of a tethered system, in which the sources of liquid and gas are in a remote unit.

Accordingly, a sprayhead arrangement has been disclosed for producing a gas-assisted spray droplet system which is sufficiently compact to comfortably fit within the mouth of a user, while at the same time the gas and liquid flow rates and velocities to the sprayhead are within a range which is comfortable and safe, but still effective for oral cleaning.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A droplet spray generating apparatus for use in an oral cleaning device, comprising:

a sprayhead housing (60) having an orifice plate (62) therein with at least one orifice opening (64) therethrough;

a source of liquid;

a liquid line system (36) for delivering liquid from the source of liquid to the sprayhead housing, above the orifice plate, wherein the liquid flow rate through the orifice opening is sufficiently great relative to the size of the orifice opening that the liquid moves through the orifice opening and exits therefrom as a stream of liquid;

a source of gas; and a gas line system (38) for delivering gas from the source of gas to the sprayhead housing, through at least two openings in the sprayhead housing, wherein the two openings are downstream of the orifice opening, said two openings being oriented such that the gas flow therefrom impacts the liquid stream from the orifice opening approximately 180° apart and wherein the gas flow strikes the liquid stream approximately perpendicularly, wherein the sprayhead housing includes a droplet acceleration portion (66) downstream from the sprayhead housing portion and downstream from the two openings in the sprayhead housing, with the acceleration portion comprising an outlet duct having a diameter in the range of 0.4 to 0.6 mm, which is approximately equal to or smaller than the portion of the sprayhead housing having the gas openings; the orifice opening having a diameter in the range of 150-350 μm, wherein the interior of the sprayhead is structured and arranged relative to the gas flow through the gas opening such that the gas flow strikes the liquid stream from the orifice opening with a velocity and flow rate sufficient to break up the liquid stream into a spray of droplets having sufficient size and sufficient velocity, in the range of 25-70 meters per second, to produce cleaning of the teeth.

2. The droplet spray apparatus of claim 1, wherein pressure generated by the liquid flow is larger than pressure necessary to overcome the surface tension of the liquid.

3. The droplet spray apparatus of claim 1, wherein the orifice plate is made of a material which includes silicon.

4. The droplet spray apparatus of claim 1, wherein the orifice plate includes a plurality of orifice openings.

5. The droplet spray apparatus of claim 1, wherein the diameter of the acceleration duct is approximately 0.4 mm and the diameter of the orifice opening is in the range of 150-200 μm.

* * * * *